United States Patent
Kim et al.

(10) Patent No.: US 11,612,462 B2
(45) Date of Patent: Mar. 28, 2023

(54) METHOD OF IMPLANTING DENTAL RESTORATION

(71) Applicant: DIO Corporation, Busan (KR)

(72) Inventors: Jin Cheol Kim, Yangsan-si (KR); Jin Baek Kim, Busan (KR)

(73) Assignee: DIO CORPORATION, Busan (KR)

(*) Notice: Subject to any disclaimer, the term of this patent is extended or adjusted under 35 U.S.C. 154(b) by 267 days.

(21) Appl. No.: 17/095,840

(22) Filed: Nov. 12, 2020

(65) Prior Publication Data

US 2022/0054238 A1 Feb. 24, 2022

(30) Foreign Application Priority Data

Aug. 24, 2020 (KR) .................. 10-2020-0106081
Aug. 24, 2020 (KR) .................. 10-2020-0106085

(51) Int. Cl.
| | | |
|---|---|---|
| *A61C 13/225* | (2006.01) | |
| *A61C 13/12* | (2006.01) | |
| *A61C 13/00* | (2006.01) | |
| *A61C 13/107* | (2006.01) | |
| *A61C 1/08* | (2006.01) | |
| *A61C 8/00* | (2006.01) | |

(52) U.S. Cl.
CPC .......... *A61C 13/0001* (2013.01); *A61C 1/084* (2013.01); *A61C 8/0095* (2013.01); *A61C 13/0004* (2013.01); *A61C 13/12* (2013.01); *A61C 13/2255* (2013.01); *A61C 8/009* (2013.01)

(58) Field of Classification Search
CPC .. A61C 13/2255; A61C 13/0001; A61C 1/082
See application file for complete search history.

(56) References Cited

U.S. PATENT DOCUMENTS

| | | | | |
|---|---|---|---|---|
| 2011/0046684 | A1* | 2/2011 | Abdelgany | A61B 17/7037 606/305 |
| 2014/0134566 | A1* | 5/2014 | Lemke | A61C 9/004 433/29 |
| 2015/0010881 | A1* | 1/2015 | Llop | A61C 8/0089 433/215 |
| 2016/0287336 | A1* | 10/2016 | Kim | A61B 6/032 |
| 2018/0042709 | A1* | 2/2018 | Savic | A61C 13/1003 |

FOREIGN PATENT DOCUMENTS

WO  WO-2007015140 A2 *  2/2007  ............. A61C 1/084

* cited by examiner

*Primary Examiner* — Amy R Sipp
*Assistant Examiner* — Courtney N Huynh
(74) *Attorney, Agent, or Firm* — Lex IP Meister, PLLC

(57) ABSTRACT

In order to improve the reliability of a dental restoration, a method of implanting the dental restoration is provided. The method includes virtually disposing a virtual implant selected from a digital library on the basis of a CT image to correspond to an implantation information, and a virtual implanting guide sleeve, which is virtually and concentrically disposed to be spaced upward from an upper end portion of the virtual implant by an offset distance, and a scanning image overlap and are integrally stored; and generating design information of a surgical guide, wherein a virtual coupling hole corresponding to an outer circumference of the virtual implanting guide sleeve is formed in the design information.

14 Claims, 10 Drawing Sheets

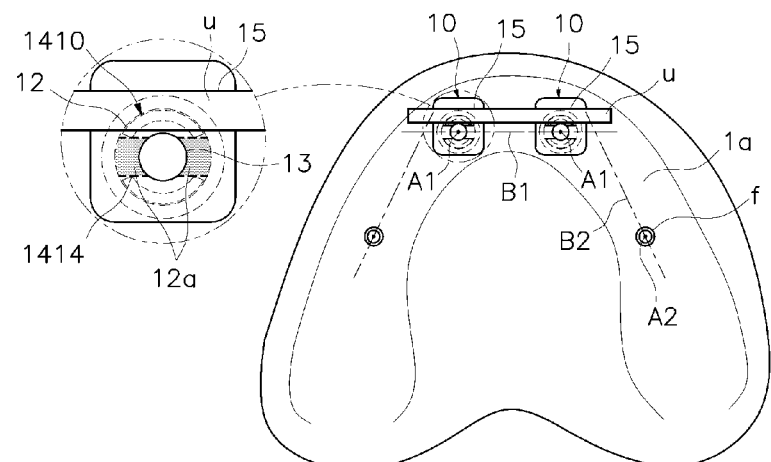
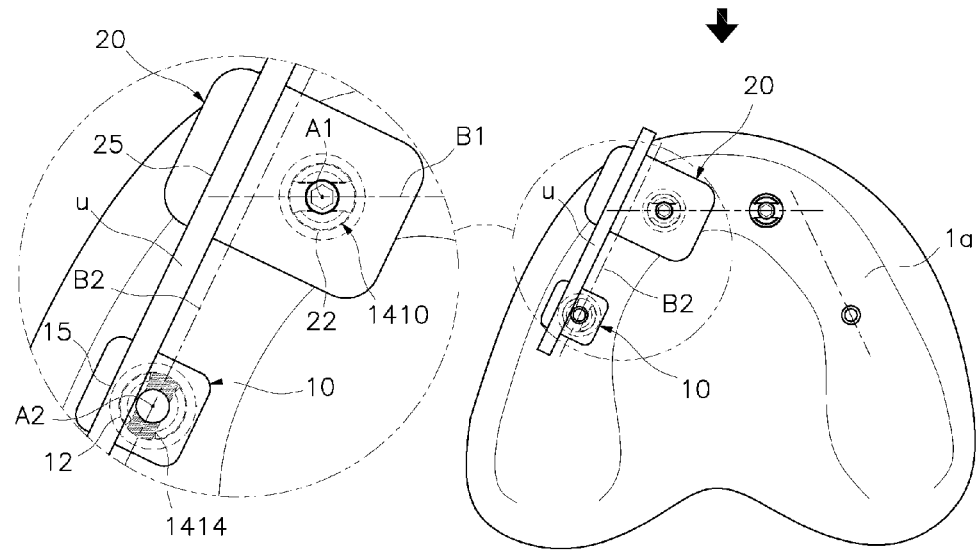
FIG.11A
FIG.11B (a)

(b)

METHOD OF IMPLANTING DENTAL RESTORATION

CROSS-REFERENCE TO RELATED APPLICATION

This application claims the benefit of Korean Application Nos. 10-2020-106081 and 10-2020-106085 which were respectively filed on Aug. 24, 2020, which were hereby incorporated by reference as if fully set forth herein.

BACKGROUND

1. Field of the Invention

The present invention relates to a method of implanting dental restoration, and more specifically, to a method of implanting dental restoration for improving reliability of dental restoration.

2. Discussion of Related Art

Generally, dentures or dental prostheses are dental restorations which artificially replace missing natural teeth to restore external form and functions thereof. In this case, the denture or dental prostheses is mounted in an oral cavity to restore a masticatory function and prevent deformation of periodontal tissue. The denture or dental prostheses may be divided into partial/full dentures or partial/full dental prostheses according to the number of missing teeth.

Meanwhile, a dental adhesive is applied on an engaging groove in an inner side of the denture and the denture is attached to and mounted on a surface of a gum. Accordingly, since an occlusal pressure is directly applied to the gum, there is a problem of causing a strange sensation and pain. However, since the dental prostheses are fixed to fixtures implanted in an alveolar bone, a strange sensation and pain of a gum due to an occlusal pressure are reduced. However, there is a problem in that it is difficult to manage the dental prostheses because the dental prostheses are actually and permanently fixed in the oral cavity. Therefore, an overdenture configured to compensate for disadvantages of the dentures and the dental prostheses has been disclosed.

Specifically, since the overdenture is fixed to the fixtures implanted in the alveolar bone like the dental prostheses and is also detachable from the oral cavity like the denture, maintenance, such as cleaning, is easy. In this case, the overdenture includes coupling parts selectively coupled to abutments or attachments coupled to the fixtures.

In this case, the conventional coupling parts are provided as ball type coupling parts individually matching to a plurality of attachments spaced apart from each other and fixedly implanted along a dental arch of the alveolar bone, or bar type coupling parts passing abutments.

Specifically, the ball type coupling parts have structures in which upper end portions of the attachments are individually coupled to fixing parts formed on an inner surface of the overdenture. That is, positional precision between the attachments and the fixing parts is required, and there is a problem in that the overdenture is not accurately mounted when any one of the coupling parts is not aligned with the attachment at an exact position.

In addition, in the bar type coupling parts, a fixing bar fixedly passes along the abutments, and mounting grooves into which the upper end portions of the abutments and the fixing bar are inserted are formed on the inner surface of the overdenture. Accordingly, the bar type coupling part has an advantage in that the overdenture is easily mounted in the oral cavity when compared to the ball type coupling part.

In this case, the fixing bar is provided to be bent to correspond to implantation information of the fixtures so as to pass the plurality of the abutments and is formed of a metal material of which deformation due to an external pressure such as a masticatory pressure may be minimized after being bent. Accordingly, in order for the fixing bar to be firmly fixed to the abutments, an implantation height of the fixture and implantation heights of the abutments should be consistently aligned, and to this end, a flattening work of the alveolar bone is required. In addition, occlusal vertical dimensions of patients requiring dental restoration are different from each other and cutting amounts of alveolar bones are determined according to the occlusal vertical dimensions.

However, since an operator conventionally cuts/flattens the alveolar bone on the basis of experience thereof, in a case in which the cutting amount is too large or small, there is a problem in that opposing teeth and the overdenture are not properly occluded, and thus discomfort is increased. In addition, there is a problem in that a flattened outer surface of the alveolar bone is not precisely formed to correspond to the implantation height of the fixture so that the fixing bar is not firmly fixed.

Meanwhile, conventionally, an overall dental restoration plan including the implantation information and a design of the overdenture is designed on the basis of a computed tomography (CT) image including information of an outer surface, a density, and the like of the alveolar bone of the patient.

Here, in the case of the CT image, the information of the alveolar bone is easily obtained but information of soft tissues of the gum is difficult to obtain. In addition, there is a problem in that it is difficult to use CT image data to design various devices configured to guide a real overdenture and implantation. That is, when the CT image is converted to a stereo lithography (STL) file allowing the overdenture and the various guide devices to be easily three-dimensionally printed or milled, it takes an excessive amount of time. In addition, since it takes a long time to manufacture the various guide devices and to perform a series of implantation processes using the various manufactured guide devices, that is, processes of cutting the alveolar bone, implanting the fixtures, and the like, there is a problem in that an overall period of time for the dental restoration is increased, and thus discomfort is increased.

SUMMARY OF THE INVENTION

According to an aspect of the present invention, there is provided a method of implanting a dental restoration including a first operation in which a three-dimensional planning image is generated in which a scanning image overlaps and matches to a computed tomography (CT) image, a plurality of pieces of implantation information of implants are set along a dental arch in the three-dimensional planning image, and an implanting guide device is designed and manufactured, a second operation in which an alveolar bone is flattened by being guided by the implanting guide device, the implants are implanted, and a holder device including a holder abutment and a fixing bar is fixed to an upper side of the implant, a third operation in which a temporary denture is corrected to be occluded between upper and lower jaws to form a temporary mounting portion in which the holder device is inserted into an inner surface portion thereof, a fourth operation in which a corrected scanning image corrected to expose three-dimensional exterior information of the temporary mounting portion to the outside is obtained from a scanning image of the temporary denture, and the three-dimensional exterior information of the temporary mounting portion is replaced and swapped with a virtual holder device, and a fifth operation in which a mount part is formed in an inner surface portion on the basis of the virtual holder device, and an artificial tooth part is fixed to an artificial gum part to which a clip engaged with the fixing bar is fixed so as to manufacture a final dental restoration.

BRIEF DESCRIPTION OF THE DRAWINGS

Features and advantages of the present invention will be understood more clearly by describing exemplary embodiments thereof in detail with reference to the accompanying drawings, in which:

FIGS. 11A and 11B are a set of exemplary views illustrating a process of fixing a holder device according to one embodiment of the present invention;

DETAILED DESCRIPTION OF EXEMPLARY EMBODIMENTS

Figure 1:
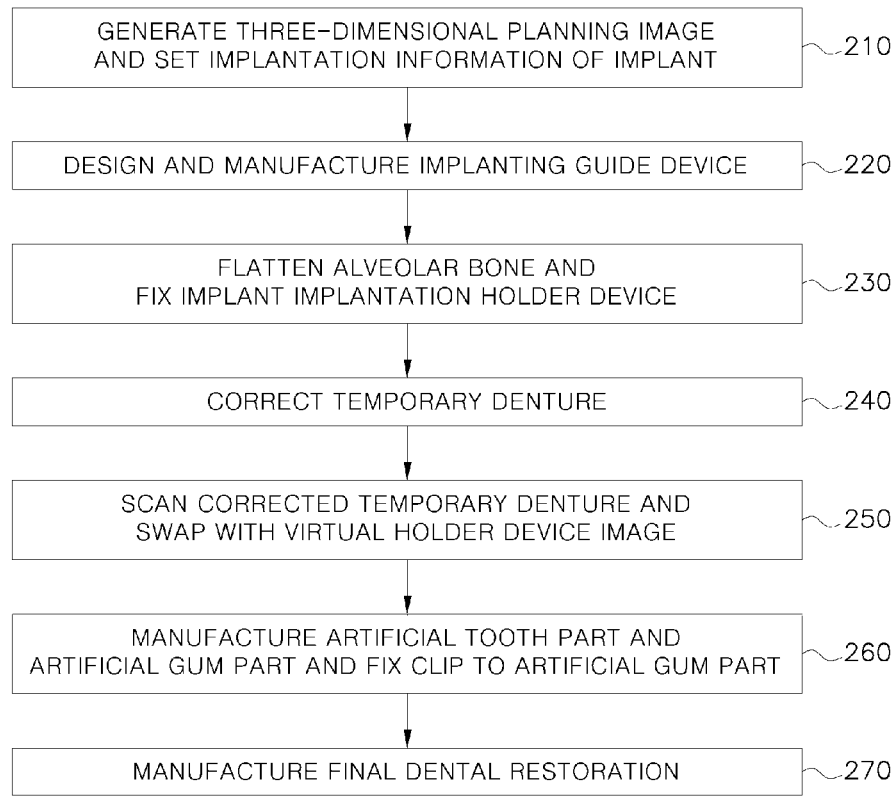
FIG. 1 is a flowchart of a method of implanting a dental restoration according to one embodiment of the present invention.

Hereinafter, methods of implanting dental restoration according to exemplary embodiments of the present invention will be described in detail with reference to the accompanying drawings.

Meanwhile, it is preferable that an implanting method of the present invention be understood as encompassing a series of processes for implanting an implant (fixture) in an alveolar bone, manufacturing a final dental restoration, and mounting the final dental restoration on an upper side of the implanted fixture. In this case, it is preferable that the finally manufactured dental restoration according to the present invention be understood as an overdenture. The overdenture includes a holder abutment and a fixing bar and is detachably mounted to be spaced apart from an oral cavity through a holder device fixed to the upper side of the fixture.

In addition, it is preferable that a restoration target gum part, which will be described below, be understood as a jaw on which dental restoration is required using the overdenture and the restoration target gum part is described and illustrated as a lower jaw in which molar teeth remain in the present invention. In addition, it is preferable that an opposing dental arch or opposing side, which will be described below, be understood as a jaw occluding with the restoration target gum part, and the opposing dental arch or opposing side is described and illustrated as a dentulous upper jaw in the present invention. However, as necessary, the present invention may also be applied to an overdenture manufacturing process in the case of an edentulous or partially edentulous upper jaw and/or lower jaw and in the case of an edentulous upper jaw and/or lower jaw but requiring tooth extraction and restoration.

It is preferable that an implanting guide device, which will be described below, is understood to include a bone reduction guide and a surgical guide. It is preferable that the bone reduction guide be understood as a device configured to guide an upper end portion of the alveolar bone to be cut to match to an implantation height of the fixture. In this case, the implantation height of the fixture is set in consideration of an occlusal vertical dimension between the overdenture and the opposing tooth and a height of the holder device. In addition, it is preferable that the surgical guide be understood as a device configured to guide the fixture to be implanted in the cut and flattened alveolar bone at an accurate implantation position and in an accurate direction.

In addition, a temporary denture, which will be described below, is a first manufactured denture which is deformed by an oral cavity or impression model manufactured after obtaining an impression of the oral cavity in order to obtain design information of the dental restoration. Of course, the temporary denture is a denture temporarily useable by a patient in a dental restoration process so that usability and convenience can be remarkably improved in the dental restoration process.

Figure 2:
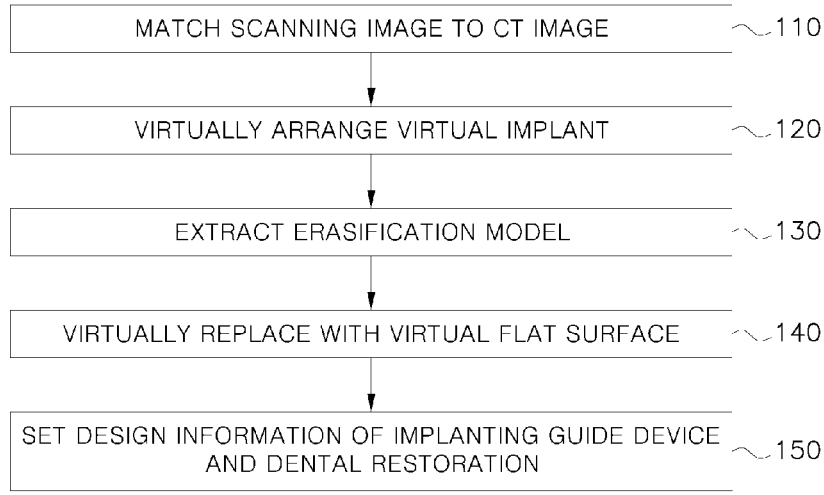
FIG. 2 is a flowchart of an image data process according to one embodiment of the present invention.
Figure 3:
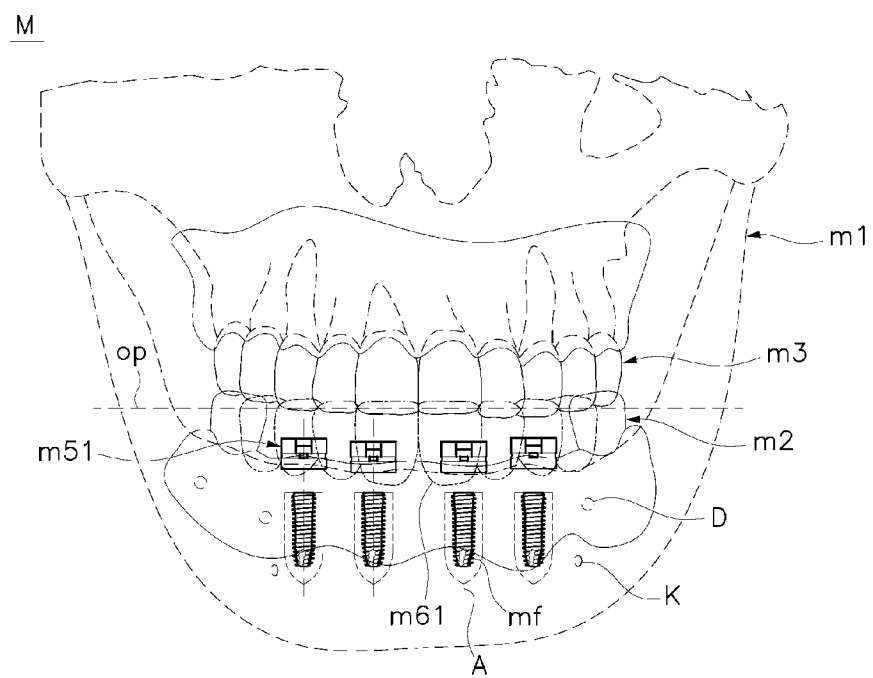
FIG. 3 is an exemplary view illustrating a three-dimensional planning image according to one embodiment of the present invention.

FIG. 1 is a flowchart of a method of implanting a dental restoration according to one embodiment of the present invention, FIG. 2 is a flowchart of an image data process according to one embodiment of the present invention, and FIG. 3 is an exemplary view illustrating a three-dimensional planning image according to one embodiment of the present invention.

Referring to FIG. 1, a method of implanting a dental restoration according to the present invention includes a series of operations such as generating a three-dimensional planning image and setting implant implantation information (210), designing and manufacturing an implanting guide device (220), flattening an alveolar bone, implanting an implant, and fixing a holder device (230), correcting a temporary denture (240), swapping a corrected scanning image (250), manufacturing an artificial tooth part and an artificial gum part and fixing a clip (260), and manufacturing a final dental restoration (270).

In addition, referring to FIG. 2, a process of processing image data in the method of implanting a dental restoration includes a series of operations such as matching a scanning image to a computed tomography (CT) image (110), virtually arranging a virtual implant (120), extracting an erasification model (130), virtually replacing a virtual flat surface (140), and setting design information of the implanting guide device and the dental restoration (150).

Specifically, referring to FIG. 3, the three-dimensional planning image M includes a scanning image obtained to include three-dimensional exterior information of upper and lower jaws of which at least one is the restoration target gum part.

Specifically, it is preferable to obtain the scanning image by scanning a surface of an oral cavity or impression model. The scanning image includes a restoration target gum part image m2 including three-dimensional exterior information of the restoration target gum part and an opposing side image m3 including three-dimensional exterior information of the opposing side. In this case, the restoration target gum part image m2 and the opposing side image m3 may be individually obtained and virtually aligned on the basis of a preset occlusal plane op. Accordingly, an upper and lower jaw image may be virtually disposed to correspond to an occlusal vertical dimension of a patient. In addition, a CT image m1 of a head of the patient is obtained using a CT imaging device and includes information of inner tissue hidden by gum tissue.

The scanning image may overlap and match to the CT image m1 on the basis of a common portion thereof, and thus the three-dimensional planning image M may be generated. Here, the common portions may be outer surfaces of hard tissue which are not hidden by the gum tissue and of which movement is also minimized and may be outer surfaces of the remaining teeth or a gap between the teeth.

Alternatively, in a case in which at least one side thereof is edentulous, a reference marker is attached thereto, the scanning image and the CT image m1 are obtained, and reference marker images displayed at the same portions of the images may be set as a common portion and match to each other. In this case, it is preferable to attach the reference marker to a lower side which is maximally spaced apart from an upper end portion of the alveolar bone in consideration of a cutting height of the alveolar bone.

Accordingly, in the three-dimensional planning image M, the three-dimensional exterior information of the restoration target gum part and the opposing side included in the scanning image and information of an inner structure such as the alveolar bone, the remaining teeth, and inferior alveolar nerve K at upper and lower jaw sides included in the CT image m1 may be simultaneously displayed. In this case, the restoration target gum part image m2, the opposing side image m3, and the CT image m1 may be displayed to overlap each other on the basis of the common portion, may be individually correctable, and may be operated to be selectively displayed or flickered. That is, it is preferable that the three-dimensional planning image M is understood to be in a state in which the scanning image and the CT image m1 are not combined and are virtually disposed only to overlap each other.

In the three-dimensional planning image M, a plurality of pieces of the implantation information A are virtually set along a dental arch. Specifically, it is preferable that one or more pieces of the implantation information A is set, and it is preferable that the implantation information A is set at four positions at a front tooth side or two positions at the front tooth side and two positions at a molar tooth side to stably mount and support the final dental restoration.

In addition, virtual teeth m61 may be virtually disposed in the three-dimensional planning image M. The virtual teeth m61 are three-dimensional exterior information of the artificial tooth part, which will be described below, and are prestored in a digital library which is a storage for storing pieces of image data for designing the dental restoration. The digital library is connected to a planning part through wired and wireless communication. In this case, it is preferable that the planning part be understood as a device in which the scanning image and the CT image m1 are loaded and displayed thereon, the three-dimensional planning image M is generated, and various pieces of design information are set thereto. That is, image data obtained through a scanner or the CT imaging device and image data stored in the digital library are loaded on the planning part to set an overall plan for the dental restoration, and the design information of the implanting guide device and the overdenture may be obtained therefrom.

It is preferable to set the virtual teeth m61 with three-dimensional vector data standardized on the basis of an average value of various teeth calculated in consideration of anatomical deviations according to gender and age. In addition, the virtual teeth m61 may be standardized to have a single size and prestored or divided as large/medium/small sizes and prestored. In addition, in the virtual teeth m61, pieces of three-dimensional exterior information of artificial teeth corresponding to teeth are preferable to individually be set and stored as units of sets along the dental arch. That is, the virtual teeth m61 may be simultaneously and virtually disposed on the three-dimensional planning image M in a state in which a plurality of tooth images of any jaw arch of the upper and lower jaws are disposed along the dental arch. In this case, the virtual teeth m61 may be modified to selectively erase an unnecessary tooth image from the tooth images.

Figure 4:
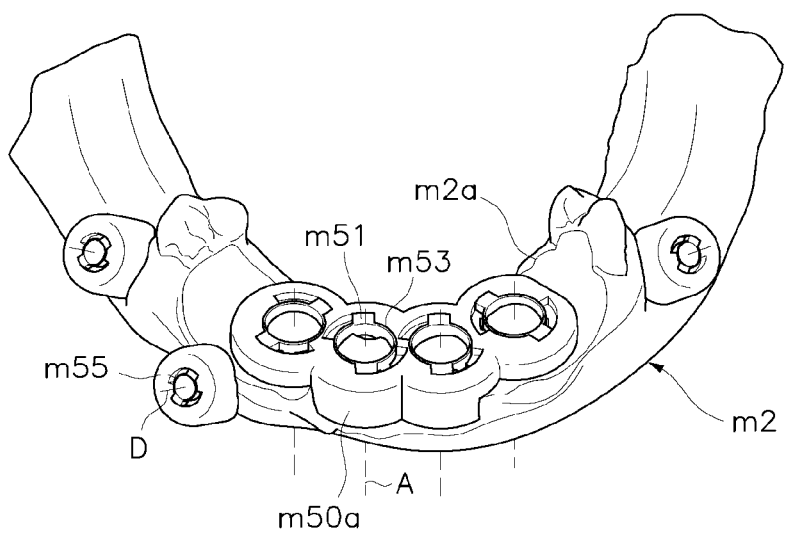
FIG. 4 is an exemplary view illustrating a virtual arrangement process of a virtual sleeve device according to one embodiment of the present invention.

FIG. 4 is an exemplary view illustrating a virtual arrangement process of a virtual sleeve device according to one embodiment of the present invention. In this case, it is preferable that the virtual sleeve device is understood to include a virtual implanting guide sleeve and a virtual fixing guide sleeve which will be described below.

Referring to FIGS. 3 and 4, virtual implants mf selected from the digital library are virtually disposed to correspond to the implantation information A. In this case, the virtual implants mf may be virtually disposed on the basis of information of the alveolar bone included in the CT image m1. In addition, the virtual implanting guide sleeves m51, which are virtually and concentrically disposed to be spaced upward from upper end portions of the virtual implants mf, and the scanning image overlap and are integrally stored.

The virtual implant mf is preferably understood as three-dimensional exterior information of a real fixture. In addition, it is preferable that the virtual implanting guide sleeves m51 be understood as three-dimensional exterior information of guide sleeves coupled to surgical guides, which will be described below, and configured to guide implantation of the real fixtures. The virtual implanting guide sleeve m51 may be prestored in the digital library as a set with the virtual implant mf. In this case, it is preferable to set an offset distance (w3 of FIG. 6) of the virtual implanting guide sleeve m51 according to a standard of the virtual implant. In this case it is preferable that the offset distance (w3 of FIG. 3) be understood as a separation distance between an upper end of the fixture and an upper end of the guide sleeve. The offset distance (w3 of FIG. 6) is set in consideration of interference with the remaining adjacent teeth or the adjacent virtual implanting guide sleeves m51.

In this case, it is preferable to set the virtual implanting guide sleeves m51 as a set with virtual coupling parts m50a which have three-dimensional exterior information of coupling parts included in the surgical guides. The virtual coupling parts m50a include virtual coupling holes m53 virtually coupled to the virtual implanting guide sleeves m51. The virtual coupling holes m53 have three-dimensional exterior information of coupling holes coupled to real guide sleeves and coupling grooves which are disposed in the coupling holes and to which protrusions of the guide sleeves are rotatably coupled.

In addition, the virtual fixing guide sleeves m55 are virtually disposed to correspond to anchor pin information D set in consideration of the implantation information A, the inferior alveolar nerve K, and the like. It is preferable that the virtual fixing guide sleeve m55 is integrally stored with the scanning image, preferably the restoration target gum part image m2, together with the virtual implanting guide sleeve m51. In this case, since a real structure of the virtual fixing guide sleeve m55 is the same as that of the virtual implanting guide sleeve m51 except a size and a position thereof, a specific description thereof will be omitted.

The virtual implanting guide sleeve m51 and the virtual fixing guide sleeve m55 overlap the scanning image and are integrally stored to be used as the design information of the implanting guide device, which will be described below, through a series of processes. In this case, since the virtual implanting guide sleeve m51, the virtual fixing guide sleeve m55, and the virtual coupling part m50a are set and prestored, a design process of the surgical guide is quick and is simplified, and thus manufacturing convenience can be significantly improved.

In this case, a process of erasing and correcting an image inside a temporary erasing line m2a preset in the restoration target gum part image m2 may be further included. For example, in a case in which the restoration target gum part image m2 includes a shape of a large number of remaining teeth or the virtual sleeve devices are excessively hidden by the restoration target gum part image m2, the erasing and correcting of the image may be performed. Accordingly, since a state in which the virtual implanting guide sleeve m51 and the virtual fixing guide sleeve m55 overlap the scanning image is displayed to be clearly visually recognized, design convenience can be further improved.

In the present invention, as described above, the implantation information A is accurately set on the basis of the CT image m1 on which an entire transverse sectional image of the oral cavity is displayed and image data actually needed for design is set on the basis of the scanning image which is surface data of targets and virtual data. Accordingly, conversion to a stereo lithography (STL) file allowing the implanting guide device, which will be described below, and the like to be quickly manufactured by three-dimensional printing is easy, and overall designing and manufacturing processes may be quickly performed.

Figure 5:
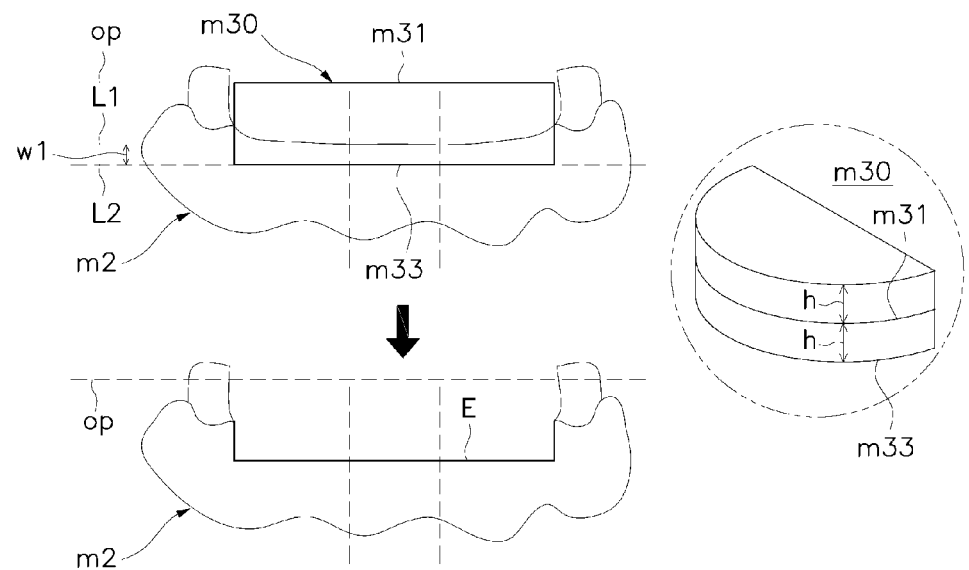
FIG. 5 is an exemplary view illustrating a setting process of a virtual flat surface according to one embodiment of the present invention.

FIG. 5 is an exemplary view illustrating a setting process of the virtual flat surface according to one embodiment of the present invention. In this case, hereinafter, it is preferable that a meaning of the three-dimensional exterior information of the restoration target gum part be understood as a meaning that is the same as that of the restoration target gum part image m2, and descriptions and illustrations thereof will use with the same number.

Referring to FIG. 5, one erasification model m30 matching to the restoration target gum part is extracted from the digital library. The erasification model m30 is standardized in a semi-cylindrical column shape corresponding to an anatomical dentition and prestored in the digital library. In this case, a rounded portion of the erasification model m30 corresponds to a mesial of the oral cavity and a vertical surface side corresponds to a distal of the oral cavity.

In the erasification model m30, a horizontal reference surface m31 matching to the occlusal plane op may cross a central portion thereof or may be set at the other surface (an upper surface in the drawing). For example, when dental restoration is simultaneously performed on the upper and lower jaws, the horizontal reference surface m31 is set along a center of the erasification model m30, and when dental restoration is performed on one side of the upper and lower jaws, the horizontal reference surface m31 may be set at the other surface of the erasification model m30. In this case, a distance h between the horizontal reference surface m31 and the one surface m33 may be virtually adjusted in consideration of the occlusal vertical dimension and the dental restoration plan of the patient.

In this case, in the erasification model m30, one surface corresponding to a side of the restoration target gum part image m2 is virtually adjusted to correspond to a second reference surface L2 spaced downward from a first reference surface L1 by a preset allowance distance w1.

Specifically, the first reference surface L1 is set to be spaced apart from the occlusal plane op to correspond to the preset occlusal vertical dimension and corresponds to the upper end portion of the virtual implant. That is, the virtual implant is selectively extracted from the digital library and virtually disposed along the dental arch, and a position of the upper end portion thereof may be virtually aligned to match to the first reference surface L1.

In this case, it is preferable to set the allowance distance w1 in consideration of positions and an arrangement angle of lower end portions of the virtual implanting guide sleeves m51 protruding downward from the first reference surface L1. That is, the allowance distance w1 may be set in consideration of three-dimensional exterior information of the virtual implanting guide sleeves m51 or the virtual coupling parts m50a protruding downward from the first reference surface L1. Accordingly, when a real surgical guide is mounted in the oral cavity to guide implantation of the fixture, interference between an inner surface structure of the surgical guide and an upper surface portion of the alveolar bone may be prevented. Accordingly, since the fixture is accurately implanted to correspond to the implantation information A set on the basis of the three-dimensional planning image M, implantation precision can be significantly improved.

Meanwhile, in the restoration target gum part image m2, a portion overlapping the erasification model m30 is erased to form the virtual flat surface E, and an upper end portion of the restoration target gum part image m2 is virtually swapped with the virtual flat surface E. Accordingly, overall design information of the implanting guide device may be quickly and accurately set on the basis of the three-dimensional exterior information of the restoration target gum part, the virtual implanting guide sleeve m51, and the virtual flat surface E.

Figure 6:
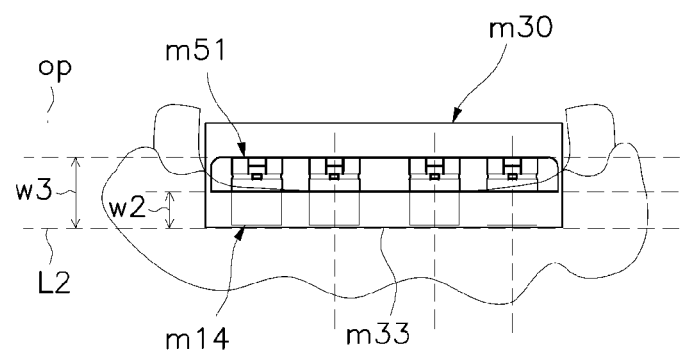
FIG. 6 is an exemplary view illustrating a modified example of the setting process of the virtual flat surface according to one embodiment of the present invention.

FIG. 6 is an exemplary view illustrating a modified example of the setting process of the virtual flat surface according to one embodiment of the present invention. In this case, since an actual structure of the present modified example is the same as that of one embodiment excluding a process in which the erasification model is virtually disposed, specific descriptions of the same components will be omitted.

Referring to FIG. 6, the erasification model m30 may be virtually disposed on the basis of a virtual abutment m14 correspondingly matching to the offset distance w3 of the virtual implanting guide sleeve m51. The virtual abutment m14 is virtually disposed between the virtual implanting guide sleeve m51 spaced apart therefrom in consideration of the offset distance w3 and the virtual implant. It is preferable that a lower surface portion of the virtual abutment m14 is formed in a cylindrical shape matching to the upper end portion of the virtual implant, and a height w2 thereof may be set according to the offset distance w3. For example, in a case in which the offset distance w3 is 9 mm, a length of the virtual abutment may be set as 4.5 mm, in a case in which the offset distance w3 is 10.5 mm, the length of the virtual abutment may be set as 6 mm, and in a case in which the offset distance w3 is 12 mm, the length of the virtual abutment may be set as 7.5 mm.

In addition, it is preferable that the one surface m33 of the erasification model m30 is virtually corrected to correspond to the second reference surface L2 set to correspond to a position of the lower surface portion of the virtual abutment m14. That is, the erasification model m30 is virtually disposed in consideration of a position of an upper end portion of a holder abutment coupled to an upper end of the real fixture. Accordingly, since cutting and flattening heights of the alveolar bone are more desirably set, a precision degradation problem due to interference between the oral cavity and the devices or between the devices may be prevented during an implantation process which will be described below in advance.

In addition, cutting and flattening ranges/positions of the alveolar bone are set on the basis of the virtual implant and the virtual implanting guide sleeve m51 virtually disposed as a set with the virtual implant. That is, the cutting and flattening heights of the alveolar bone may be set after the height of the holder device and a height of the overdenture mounted through the holder device are considered first. Accordingly, since occlusion precision between the overdenture that is finally manufactured and mounted in the oral cavity and the opposing teeth is improved and discomfort is minimized during mastication, satisfaction with the dental restoration can be significantly improved.

Figure 7A:
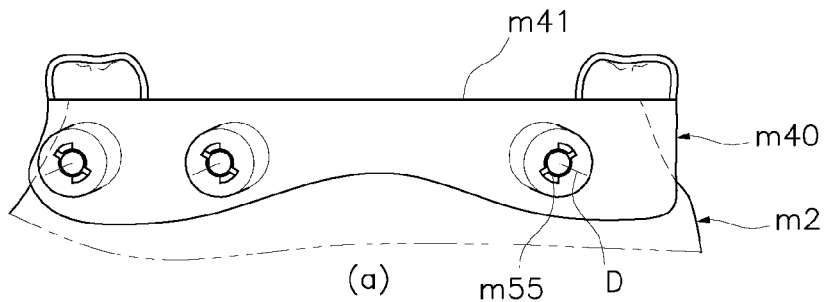
FIGS. 7A and 7B are a set of exemplary views illustrating design information of an implanting guide device according to one embodiment of the present invention.
Figure 7B:
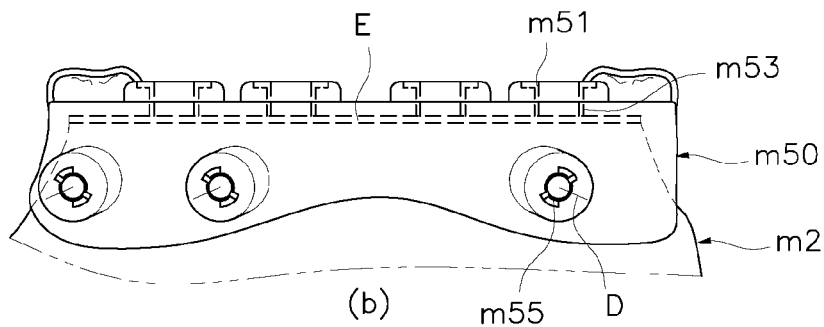

FIGS. 7A and 7B are a set of exemplary views illustrating design information of the implanting guide device according to one embodiment of the present invention.

Referring to FIG. 7A, design information m40 of the bone reduction guide is set to include an operation in which a contour of the inner surface portion of the bone reduction guide is formed on the basis of the three-dimensional exterior information of the restoration target gum part and an operation in which design information m41 of a flattening guide surface is formed along an edge opening at a position corresponding to the virtual flat surface E. In addition, the design information m40 of the bone reduction guide is transferred to a manufacturing apparatus such as a three-dimensional printer to manufacture a real bone reduction guide.

Specifically, a virtual body part is formed to protrude or be separated by a preset thickness or distance using surface data of inner and outer side surfaces of the gum corresponding to a lower side with respect to the virtual flat surface E in the restoration target gum part image m2. In this case, an upper side of the virtual body part with respect to the virtual flat surface E is set to be open. In addition, the design information m41 of the flattening guide surface is set along an upper end edge of the virtual body part matching to an edge of the virtual flat surface E. In addition, design information of a piece fixing part allowing an anchor pin to be fixed thereto on the basis of the virtual fixing guide sleeve m55 and the scanning image which overlap and are stored may be included in the design information m40 of the bone reduction guide.

Referring to FIG. 7B, design information m50 of the surgical guide is designed to form the virtual coupling holes m53 corresponding to an outer circumference of the virtual implanting guide sleeves m51 at an upper end portion of the virtual body part. In addition, the design information m50 of the surgical guide is transferred to a manufacturing apparatus to manufacture the real surgical guide.

In this case, since the virtual coupling hole m53 is included in the virtual coupling part m50a prestored as a set with the virtual implanting guide sleeve m51, the three-dimensional exterior information of the virtual coupling hole m53 can be immediately set without a separate complicated design process. In addition, since the design information m41 of the flattening guide surface is set in consideration of the allowance distance w1, a virtual cutting surface virtually set on the basis of a lower surface portion of the virtual coupling part m50a and the design information m41 of the flattening guide surface may be set to be spaced apart therefrom. In addition, the design information of the piece fixing part may also be included in the design information m50 of the surgical guide on the basis of the virtual fixing guide sleeve m55.

That is, the bone reduction guide and the surgical guide are designed on the basis of the restoration target gum part image m2 and the anchor pin information D of which pieces of image data are substantially the same. In this case, the design information m41 or a position of the flattening guide surface of the virtual fixing guide sleeve m55 is set with respect to the virtual flat surface E. Accordingly, contours of inner surface portions of the finally manufactured bone reduction guide and surgical guide may be set to be the same as a position of the piece fixing part. Accordingly, since mounting positions therebetween are substantially the same in a process in which the bone reduction guide is separated and the surgical guide is mounted, implantation precision can be significantly improved.

In addition, in the bone reduction guide, the design information m41 of the flattening guide surface is set on the basis of the second reference surface L2 in consideration of an allowance distance in consideration of interference between the cut and flattened upper end portion of the alveolar bone and the real surgical guide. Accordingly, in a state in which the real surgical guide is mounted on the alveolar bone, an inner side surface thereof is fixedly engaged with a side surface portion of the alveolar bone and an inner surface portion thereof coupled to the guide sleeve may be spaced apart from the alveolar bone. Accordingly, since implantation errors occurring when the surgical guide is not mounted at an accurate position are prevented, implantation precision can be significantly improved.

Figure 8:
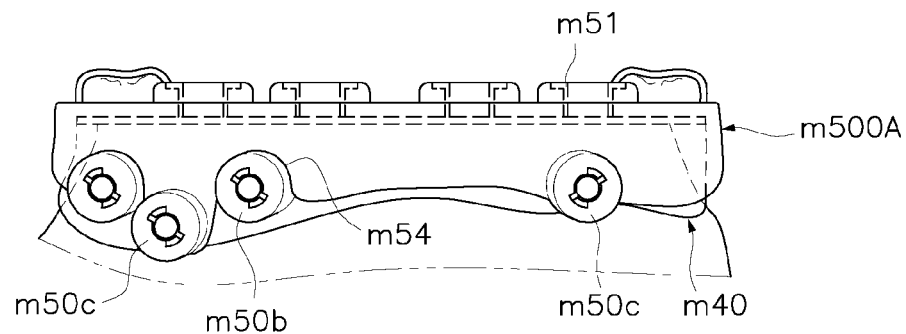
FIG. 8 is an exemplary view illustrating design information of an implanting guide device according to another embodiment of the present invention.
Figure 9:
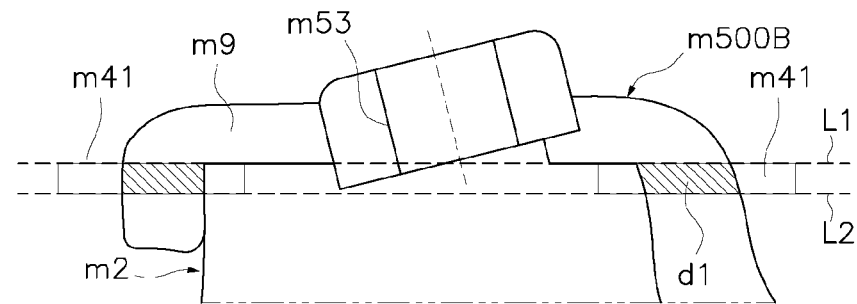
FIG. 9 is an exemplary view illustrating design information of an implanting guide device according to still another embodiment of the present invention.
Figure 10:
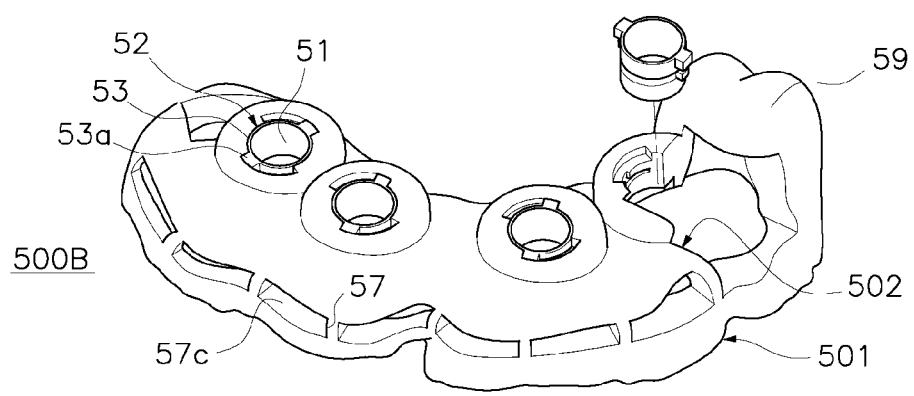
FIG. 10 is an exemplary view illustrating the implanting guide device according to still another embodiment of the present invention.

Meanwhile, FIG. 8 is an exemplary view illustrating design information of an implanting guide device according to another embodiment of the present invention, FIG. 9 is an exemplary view illustrating design information of an implanting guide device according to still another embodiment of the present invention, and FIG. 10 is an exemplary view illustrating the implanting guide device according to still another embodiment of the present invention. In this case, in FIGS. 8 and 9, since a basic structure of each of the embodiments is the same as that of one embodiment except a process of obtaining design information, specific descriptions of the same components will be omitted.

Referring to FIG. 8, in design information m500A of the surgical guide, a contour of an inner surface portion of the surgical guide may be generated based on a contour of an outer surface portion of the bone reduction guide of design information m40. In addition, the design information m500A of the surgical guide may be designed and manufactured to include an operation in which the virtual coupling hole is formed on an upper end portion thereof in the design information m500A to correspond to the virtual implanting guide sleeve m51. In this case, a virtual alignment coupling groove m54 engaging with an outer circumference of the piece fixing part in design information m50b may be set at an edge side of the surgical guide in the design information m500A. In addition, design information m50c of the piece fixing hole may also be further included in the design information m500A of the surgical guide in addition to the design information m50b of the piece fixing part included in the design information m40 of the bone reduction guide.

That is, the surgical guide designed and manufactured through the above-describe process is fixedly engaged with and supported by an outer surface side of the bone reduction guide. Accordingly, the bone reduction guide fixed to the restoration target gum part by the anchor pin may not be separated, and the surgical guide may fixedly overlap the bone reduction guide. Accordingly, since a problem, in which a mounting position of the surgical guide is misaligned in a process in which the surgical guide is mounted after the bone reduction guide is separated therefrom, is fundamentally solved, precision can be further improved. In addition, excessive damage due to the anchor pin being repeatedly implanted in and separated from the alveolar bone is prevented, and strength reduction of the alveolar bone is prevented so that safety can be significantly improved.

Alternatively, referring to FIGS. 9 and 10, a contour of an inner surface portion of a virtual guide body part m9 is formed on the basis of three-dimensional exterior information of the restoration target gum part, and the virtual guide body part m9 is set in which the virtual coupling hole m53 corresponding to the outer circumference of the virtual implanting guide sleeve is formed. In addition, a plurality of virtual cut blocks m41 which protrude to have a thickness and have a three-dimensional form so that one surfaces match to the first reference surface L1 and the other surfaces match to the second reference surface L2 are virtually disposed along a circumference of the virtual guide body part m9. Then, when an overlapping region dl of the virtual cut block m41 and the virtual guide body part m9 is erased, design information m500B of the surgical guide including design information of a cut slot hole is generated.

In addition, a real surgical guide 500B manufactured on the basis of the design information m500B of the surgical guide is divided into a first body part 501 at a lower side from cut slot holes 57 formed based on the virtual cut block m41 and a second body part 502 at an upper side therefrom. In this case, coupling holes 53 coupled to guide sleeves 52 including guide holes 51 may be formed in the second body part 502, and coupling grooves 53a in which protrusions of the guide sleeves 52 are hooked may be formed in inner circumferences of the coupling holes 53. In addition, in a case in which the molar teeth remain, an alignment engagement part 59 engaged and aligned therewith may further formed.

In addition, after two surgical guides 500B are manufactured, an upper side of one surgical guide 500B may be separated along the cut slot holes 57 so that the surgical guide 500B may be changed into a bone reduction guide. As described above, since only one instance of design is actually required to manufacture the surgical guide and the bone reduction guide, simplification and speed of a design process can be significantly improved. In addition, since lower surfaces 57c of the cut slot holes 57 are formed to actually correspond to the second reference surface L2, the lower surfaces 57c of the cut slot holes 57 may function as the flattening guide surfaces only by separating the second body part 502.

FIGS. 11A and 11B are a set of exemplary views illustrating a process of fixing a holder device according to one embodiment of the present invention, and FIGS. 12A to 12D are a set of exemplary views illustrating a process of confirming a bending angle of a fixing bar according to one embodiment of the present invention;

Referring to FIGS. 11A to 12D, the alveolar bone is guided by the bone reduction guide to be cut and flattened, and the fixtures f are implanted in the alveolar bone 1a guided by the surgical guide and cut and flattened. In addition, the holder device 1400 of FIG. 13 is fixed to the upper side of the fixture f. In this case, the holder devices 1400 of FIG. 13 include holder abutments 1410 and a fixing bar 1430.

The holder abutments 1410 are fixed to the upper sides of the fixtures f through coupling screws 1420 of FIG. 13 and through-insertion portions 1414 are formed to be recessed in the upper end portions thereof in a longitudinal direction. In this case, the fixing bar 1430 is inserted into the through-insertion portions 1414, and pressing parts 1440 of FIG. 13 are coupled to upper end portions of coupling holes 1413 of FIG. 13 of central portions through which the coupling screws 1420 pass so that the fixing bar 1430 is fixedly clamped between lower ends of inner sides of the through-insertion portions 1414 and the pressing parts 1440 of FIG. 13.

In this case, the fixing bar 1430 is bent to intersect with two implantation points A1 at the front tooth side and two implantation points at the molar tooth side of a plurality of pieces of the implantation information set along the dental arch. In this case, both end portions of the fixing bar 1430 may be bent at preset bending points so that the fixing bar 1430 may be provided in a trapezoidal shape.

Specifically, a central portion of the fixing bar 1430 is provided to intersect with the pair of implantation points A1 at the front tooth side, and the both end portions thereof are provided to intersect with the implantation points A2 at the molar tooth side. Accordingly, position of the bending points and bending angles may be accurately set on the basis of the three-dimensional planning image M, and a bent state may be stably maintained. Accordingly, damage or breakage of the alveolar bone, which is due to spring back occurring after the fixing bar 1430 is conventionally bent to be rounded, can be prevented.

Meanwhile, bent passage information for guiding bending of the fixing bar 1430 is set on the basis of the three-dimensional planning image M. That is, the implantation information is set to correspond to the pair of implantation points A1, which intersect with a central line B1 in the bent passage information, at the front tooth side and the pair of implantation points A2, which intersect with both side lines B2 in the bent passage information, at the molar tooth side. In addition, fixing zig bases 10 and pivot guide zig bases 20 configured to guide the through-insertion portions 1414 of the holder abutments 1410 to be open to correspond to the bent passage information are prepared.

Referring to FIG. 11A, the fixtures f are implanted at the implantation points A1 and A2, and the holder abutments 1410 are disposed on the upper ends of the fixtures f implanted to correspond to the pair of implantation points A1 at the front tooth side. In addition, the fixing zig bases 10 are coupled to upper ends of holder abutments 1410.

In the fixing zig bases 10, alignment protrusions 12*a* engaged with the through-insertion portions 1414 are formed on inner circumferences of accommodation grooves 12 into which the upper end portions of the holder abutments 1410 are inserted. In addition, alignment grooves 15 are formed to cross upper surfaces of the fixing zig bases 10 to be parallel to the alignment protrusions 12*a*, and through holes 13 communicating with the accommodation grooves 12 are formed in the upper surfaces thereof. Accordingly, when the alignment grooves 15 of the fixing zig bases 10 are rotated and aligned to linearly communicate with each other, opening directions of the through-insertion portions 1414 engaged with the alignment protrusions 12*a* may also be rotated and aligned to linearly communicate with each other.

In a state in which the alignment grooves 15 are rotated and aligned to linearly communicate with each other, an alignment fixing bar u is simultaneously inserted thereinto and the rotated and aligned state thereof is restricted. In addition, when a rotating device such as a driver is inserted into the through holes 13 of the fixing zig bases 10 of which rotation is restricted and when the coupling screws 1420 are coupled to the fixtures f, the holder abutments 1410 are fixed to the front tooth side.

Referring to FIG. 11B, the pivot guide zig bases 20 are replaced and coupled to the holder abutments 1410 fixed to the front tooth side. Alignment grooves 25 are formed in upper surface portions of the pivot guide zig bases 20 and accommodation grooves 22 having a cylindrical shape into which the upper end portions of the holder abutments 1410 are inserted are formed on the upper surface portions thereof. Accordingly, the pivot guide zig bases 20 may be rotatably supported by the holder abutments 1410 in a state in which the pivot guide zig bases 20 are coupled to the holder abutments 1410.

The holder abutments 1410 are disposed at the upper sides of the fixtures f implanted in the molar tooth side implantation points A2, and the fixing zig bases 10 are coupled to the holder abutments 1410. In addition, the alignment grooves 15 of the fixing zig bases 10 disposed at the molar tooth side and the alignment grooves 25 of the pivot guide zig bases 20 disposed at the front tooth side are rotated and aligned to linearly communicate with each other. Then, the alignment fixing bar u is simultaneously inserted into the alignment grooves 15 of the fixing zig bases 10 and the pivot alignment grooves 25 of the guide zig bases 20 so that the rotated and aligned states thereof are restricted. Accordingly, in the holder abutments 1410 at the molar tooth sides, the through-insertion portions 1414 may be fixedly aligned to correspond to the both lines B2.

In the fixing zig bases 10 and the pivot guide zig bases 20, it is preferable that inner circumferential diameters of the accommodation grooves 12 and 22 and separation distances between the accommodation grooves 12 and 22 and the alignment grooves 15 and 25 are standardized to correspond to a standard of the holder abutment 1410 and a unit of a bending angle of the fixing bar 1430 so as to be prepared for general purpose.

Accordingly, since cumbersomeness of individually designing and manufacturing the jig bases for fixing the holder abutments 1410 in accurate directions for each patient is minimized, an overall process and time for the dental restoration are reduced, and a cost is reduced so that it is economical. In addition, in a state in which alignment directions of the adjacent zig bases are restricted by the alignment fixing bar u to be parallel to the preset bent passage information, coupling of the coupling screws is guided. Accordingly, since coupling tolerances between the holder abutments 1410 and the fixing bar 1430 are substantially close to zero, implantation precision can be significantly improved.

Figure 12A:
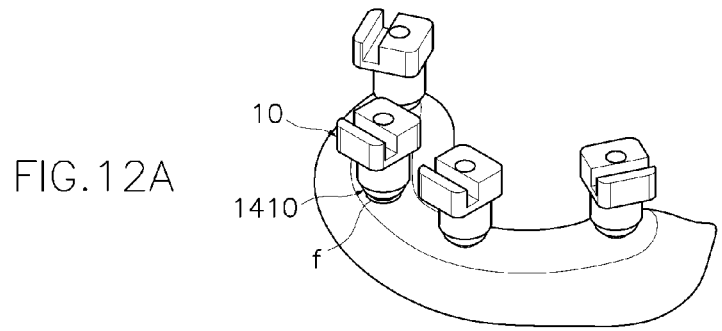
FIGS. 12A to 12D are a set of exemplary views illustrating a process of confirming a bending angle of a fixing bar according to one embodiment of the present invention.
Figure 12B:
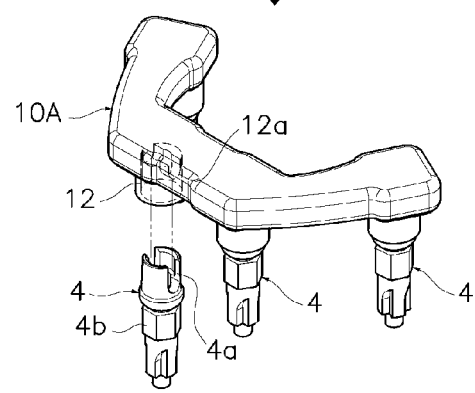
Figure 13:
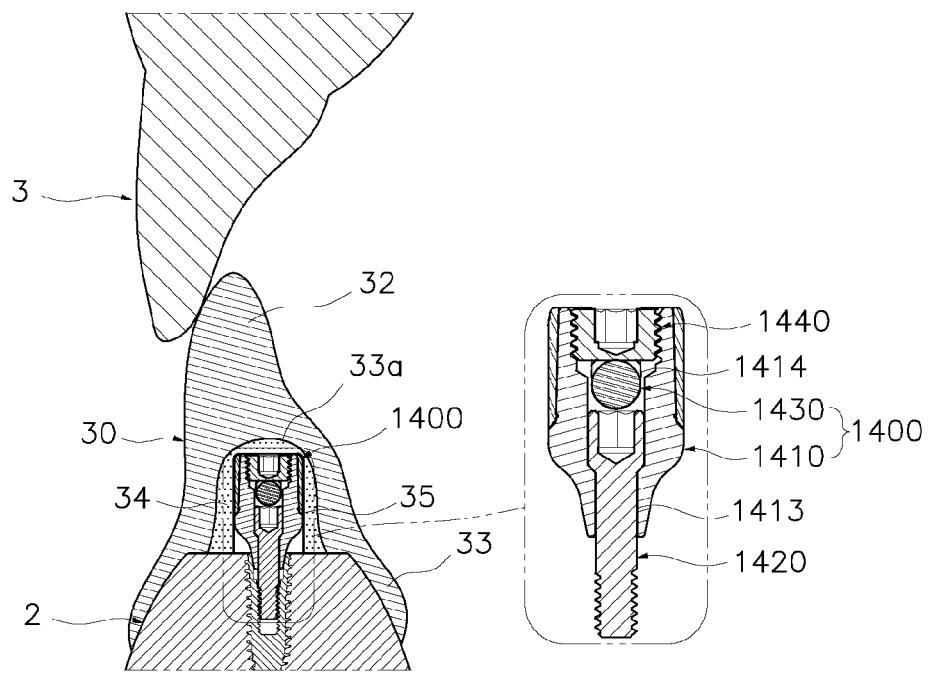
FIG. 13 is an exemplary view illustrating a correction process of a temporary denture according to one embodiment of the present invention.

Referring to FIGS. 12A and 12B, the fixing zig bases 10 are recoupled to the upper end portions of the holder abutments 1410 fixedly coupled to the fixtures f. In this case, a curable resin is applied on upper end portions of the fixing zig bases 10 to have a predetermined thickness so as to simultaneously cover the upper end portions thereof. In addition, the curable resin is cured to form an alignment support part 10A as a bridge integrally connecting the plurality of the fixing zig bases 10. That is, positions of the fixing zig bases 10 and alignment directions of the alignment protrusions 12*a* may be fixed by the alignment support part 10A.

In addition, holder analogs 4 are inserted into the accommodation grooves 12 of the fixing zig bases 10 fixed by the alignment support part 10A. Angle alignment parts 4*a* corresponding to the through-insertion portions 1414 of FIG. 13 are formed on upper end portions of the holder analogs 4. Accordingly, when the upper end portions of the holder analogs 4 are inserted into the accommodation grooves 12, the angle alignment parts 4*a* are engaged with the alignment protrusions 12*a*.

Figure 12C:
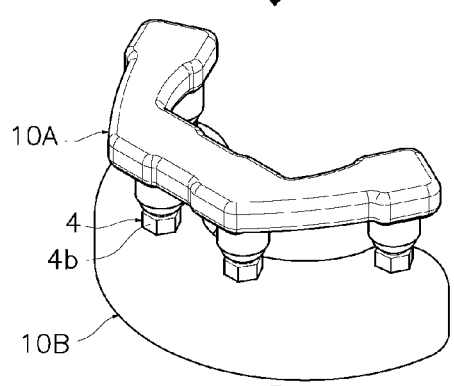

Referring to FIG. 12C, lower end portions of the holder analogs 4 aligned with and inserted into the accommodation grooves 12 are integrally connected by a curable material such as plaster. In addition, when the curable material is cured, the curable material has strength allowing separation distances between the lower end portions of the holder analogs 4 to be maintained. Accordingly, an angle confirmation model 10B may be formed in which the holder analogs 4 are restricted in a state in which the holder analogs 4 are disposed to correspond to the implantation points. In addition, restriction alignment surfaces 4*b* formed as non-continuous surfaces, such as D-cut surfaces, are formed on outer circumferences of the holder analogs 4. Accordingly, the curable material fills between lower portions of the holder analogs 4 and is cured to restrict rotation of the holder analogs 4.

Figure 12D:
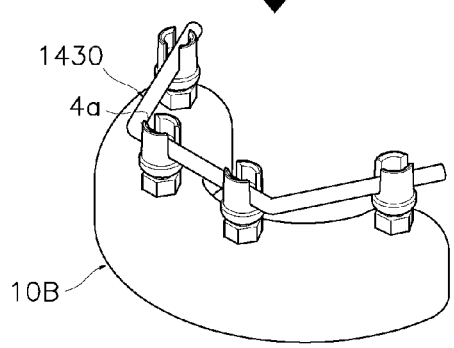

Referring to FIG. 12D, the bending angles of the fixing bar 1430 are confirmed by the angle confirmation model 10B. That is, when the fixing bar 1430 is inserted into the angle alignment parts 4*a* without interference therebetween, it may be determined that the fixing bar 1430 is bent to have proper bending angles. However, when the fixing bar 1430 is not properly inserted into the angle alignment parts 4*a* or is interfered with the angle alignment parts 4*a* when inserted thereinto, it may be determined that bending errors occur and the fixing bar 1430 may be corrected.

As described above, since the present invention generates the angle confirmation model 10B on the basis of the holder abutments 1410 directly fixed to the alveolar bone 1*a* which are cut and flattened, the fixing bar 1430 can be precisely corrected to correspond to a real oral cavity environment. In addition, after the holder abutments 1410 are fixed to the oral cavity, since the bending errors of the fixing bar 1430 are determined and corrected outside the oral cavity, discomfort caused by frequent visits of the patient to a hospital or repeated confirmation work can be minimized.

Figure 14:
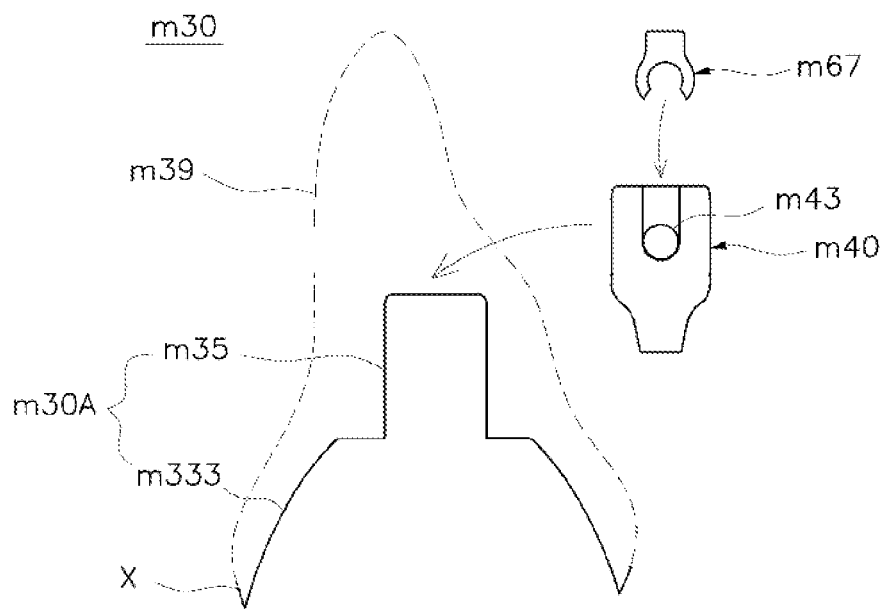
FIG. 14 is an exemplary view illustrating a process of swapping a corrected scanning image according to one embodiment of the present invention.

FIG. 13 is an exemplary view illustrating a correction process of the temporary denture according to one embodiment of the present invention, and FIG. 14 is an exemplary view illustrating a process of swapping a corrected scanning image according to one embodiment of the present invention. Meanwhile, the temporary denture 30 may be occluded with the upper and lower jaws to which the holder devices 1400 are actually fixed or with the impression model to which the holder analogs and the fixing bar are fixed and may be corrected, and hereinafter, the temporary denture 30, which is occluded with the real upper or lower jaw and corrected, will be described and illustrated as an example.

Referring to FIG. 13, the temporary denture 30 is prepared that is softened when heated at a preset softening temperature and disposed between the restoration target gum part 2 to which the holder devices 1400 are fixed and the opposing dental arch 3. In addition, the temporary denture 30 is occluded and corrected to be deformed by an occlusal pressure of the patient to correspond to the occlusal vertical dimension of the patient. Accordingly, temporary mounting portions 35 into which the holder devices 1400 are inserted are pressed and formed in an inner surface portion of the temporary denture 30.

Specifically, the temporary denture 30 may be manufactured by three-dimensionally printing to correspond to the form of the temporary denture 30 using a base resin including acrylic oligomer. The temporary denture 30 is formed to include allowance grooves 33*a* formed in an inner surface side thereof and having spaces greater than volumes of the holder devices 1400. When the temporary denture 30 is heated, it is preferable that an inner surface side of a temporary gum part 33, excepting temporary tooth parts 32 occluding the opposing teeth, is heated and softened. In addition, the temporary denture 30 may be occluded and corrected between the upper and lower jaws in a state in which the allowance grooves 33*a* are filled with a relining resin 34.

Accordingly, the temporary mounting portions 35 corresponding to forms of outer surfaces of the holder devices 1400 may be engraved in the relining resin 34, and a side of the temporary gum part 33 may be corrected to correspond to forms of outer surfaces of real dental arch and gum part of the patient. In addition, as the corrected temporary denture 30 is optically cured, the temporary denture 30 may be completely cured to withstand the masticatory pressure. Accordingly, the temporary denture 30 can be temporarily used before the dental restoration is initially manufactured.

Referring to FIG. 14, inner and outer surface portions of the temporary denture 30, in which the temporary mounting portions 35 are formed and corrected in the inner surface portions thereof, are scanned to obtain a temporary denture image m300. In addition, in the temporary denture image m300, a corrected scanning image m30A which is corrected to externally expose three-dimensional exterior information m35 of the temporary mounting portion and three-dimensional exterior information m333 of an inner surface portion of the restoration target gum part corrected to correspond to the temporary gum part is obtained.

Specifically, a boundary line X is set between the three-dimensional exterior information of the temporary gum part and the three-dimensional exterior information of the temporary tooth part. In addition, unnecessary image data excepting a portion inside the boundary line X is set as an erasification region m39 and erased. Accordingly, the three-dimensional exterior information m35 of the temporary mounting portions formed in the inner surface side of the temporary denture is swapped to be externally exposed and obtained as the corrected scanning image m30A.

In this case, it is preferable that the corrected scanning image m30A is replaced and swapped with the virtual holder device m40 prestored in the digital library. It is preferable that the virtual holder device m40 corresponds to an external form of the holder abutment 1410 and includes a virtual fixing bar m43 and a virtual clip m67 virtually engaged with the virtual fixing bar m43. That is, surface irregularities or notches generated during occlusion of the temporary denture 30 or distortion or noise which may occur during a machining or processing of scanning the temporary denture 30 can be reduced due to the swapping with the virtual holder device m40 so that design accuracy and precision can be significantly improved.

In addition, an overall scanning image including the temporary denture image m300 is stored as surface information without having thicknesses thereof. In addition, virtual data stored in the digital library is prestored therein as data usable as design information. Accordingly, since the scanning image or the corrected scanning image m30A may be easily used as design information of the overdenture, and a difficulty in an image processing is lowered and a speed is increased, design convenience can be significantly improved.

Figure 15:
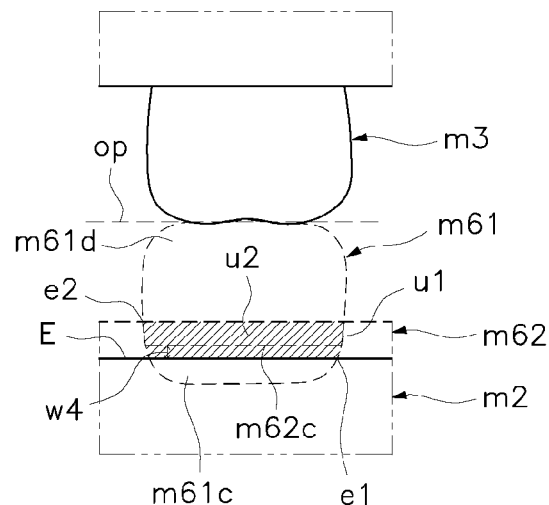
FIG. 15 is an exemplary view illustrating a design process of an overdenture and a cutting guide according to one embodiment of the present invention.
Figure 16A:
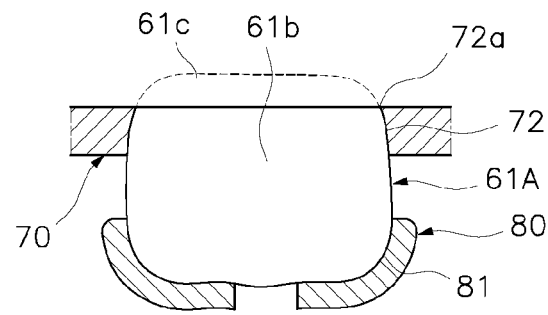
FIGS. 16A and 16B are a set of exemplary views illustrating a manufacturing process of the overdenture according to one embodiment of the present invention.
Figure 16B:
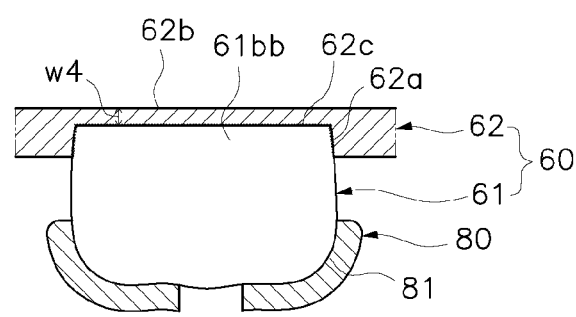

FIG. 15 is an exemplary view illustrating a design process of the overdenture and a cutting guide according to one embodiment of the present invention, and FIGS. 16A and 16B are a set of exemplary views illustrating a manufacturing process of the overdenture according to one embodiment of the present invention.

Referring to FIGS. 15 to 16B, it is preferable that a cutting guide 70 is designed and manufactured on the basis of the three-dimensional planning image M to adjust a height of the artificial tooth part 61 so as to match to the occlusal vertical dimension of the patient.

Referring to FIG. 15, the virtual teeth m61 are virtually disposed between the restoration target gum part image m2 including the virtual flat surface E and the opposing side image m3, and a virtual artificial gum part m62 is set to overlap dental root sides of the virtual teeth m61.

The virtual artificial gum part m62 may be set by selectively extracting data from data prestored in the digital library and virtually arranging the extracted data on the scanning image or set on the basis of the restoration target gum part image m2. In this case, it is preferable that the artificial tooth part 61 is standardized and provided as a ready-made product and it is preferable that the virtual tooth m61 is understood as the three-dimensional exterior information of the artificial tooth part 61 prepared as the ready-made product is prestored in the digital library. Accordingly, inconvenience of complicatedly designing and individually manufacturing artificial teeth of the artificial tooth part 61 can be minimized and a manufacturing process and a manufacturing period of the overdenture 60 can be reduced.

Meanwhile, an occlusion end portion m61d of the virtual tooth m61 is aligned with the opposing side image m3 on the basis of the occlusal plane op to be virtually occluded with the opposing side image m3. In this case, when a height of the virtual tooth m61 exceeds the occlusal vertical dimension of the patient, a dental root end portion m61c of the virtual tooth m61 protrudes downward in exterior information of the restoration target gum part image m2. In addition, a virtual base gum part m62, of which an inner surface portion corresponds to the restoration target gum part image m2, is virtually disposed on the scanning image, and a portion in which the virtual tooth m61 and the virtual base gum part m62 overlap and intersect with each other is set as a delete region u2.

That is, intersection lines e1 and e2 are set along edges formed where inner and outer surface sides of the virtual base gum part m62 in surface data thereof intersect with the virtual tooth m61 in surface data thereof, and an image, which is positioned inside the intersection lines e1 and e2, of the virtual base gum part m62 is erased. Simultaneously, an image, which is positioned outside the intersection lines e1 and e2, of the virtual tooth image m61 is erased, and an image, which is positioned inside thereof, of the virtual tooth image m61 is integrated with the virtual base gum part m62. Accordingly, a virtual engagement surface u1 may be set along an inner circumference of the delete region u2.

In this case, design information of the cutting guide includes three-dimensional exterior information of a cutting hole formed to pass through and correspond to the virtual engagement surface u1. In addition, the virtual artificial gum part, of which an inner circumference is formed on the basis of the virtual engagement surface u1, includes the inner surface information m62c of a contour of the inner surface portion of the virtual base gum part m62 that is a coupling groove spaced apart from the virtual flat surface E by a preset seating distance w4. That is, the design information of the cutting guide and the virtual artificial gum part are designed on the basis of the virtual base gum part m62, which is the same design data, and the three-dimensional exterior information of the cutting hole is formed to pass through the virtual base gum part m62 to correspond to the virtual engagement surface u1. In addition, the virtual artificial gum part may be set to be shielded by a thickness corresponding to the inner surface information m62c of the coupling groove in the virtual engagement surface u1. The design information of the cutting guide and the virtual artificial gum part which set on the basis of the three-dimensional planning image are transferred to the manufacturing apparatus to manufacture the real cutting guide 70 and a real artificial gum part 62.

Referring to FIG. 16A, the artificial teeth 61b of the artificial tooth part 61A prepared for general purpose are inserted into the cutting holes 72 of the cutting guide 70. In this case, when one side of an outer circumference of the artificial teeth 61b is hooked on and engaged with an inner circumferential surface of the cutting hole 72, the dental root end portion 61c of the artificial tooth part 61A protrudes in a direction toward the inner surface portion of the cutting guide 70. The dental root end portion 61c of the artificial tooth part 61A protruding as described above may be cut and corrected on the basis of an inner edge 72a of the cutting hole 72. Accordingly, the height of the artificial tooth part 61 may be corrected to correspond to the occlusal vertical dimension of the patient.

Referring to FIG. 16B, when artificial teeth 61bb of the cut and the corrected artificial tooth part 61 are engaged with and bonded to coupling grooves 62a of an artificial gum part 62 using an adhesive, the overdenture 60 which is the final dental restoration is manufactured. In this case, the inner surface portion 62b of the artificial gum part 62 is engaged with the restoration target gum part, and a mount part is formed. In this case, a gap between a bottom surface 62c of the coupling groove 62a and the inner surface portion 62b of the artificial gum part 62 may be formed to correspond to the seating distance w4. In addition, it is preferable that the artificial tooth 61bb is further corrected and cut by the seating distance w4 preset in the three-dimensional planning image M in consideration of a thickness difference between the cutting guide 70 and the artificial gum part 62 which have a step difference corresponding to the seating distance w4.

As described above, in the present invention, since the artificial tooth part 61A is prepared to have a standardized size without a complicated design process, manufacturing convenience is improved, and since the dental root end portion 61c is guided by the cutting guide 70 manufactured on the basis of the three-dimensional planning image M, the artificial tooth part 61A is cut and corrected to be suitable to the occlusal vertical dimension of the patient. Accordingly, since the artificial tooth part 61A is corrected to be suitable to the occlusal vertical dimension of the patient, economic feasibility and precision of the dental restoration can be significantly improved.

In this case, it is preferable that index zigs 80 are further manufactured to simultaneously align the artificial teeth 61b of the artificial tooth part 61A. In the index zigs 80, alignment zig grooves 81 are formed on the basis of three-dimensional exterior information of the occlusion end portion m61d of the virtual tooth displayed on the three-dimensional planning image M. Accordingly, since the artificial teeth 61b and 61bb are simultaneously aligned and coupled between the index zigs 80 and the cutting guide 70/artificial gum part 62, cutting of the artificial teeth 61b and attachment of the artificial teeth 61bb can be quickly guided to precise positions.

Figure 17:
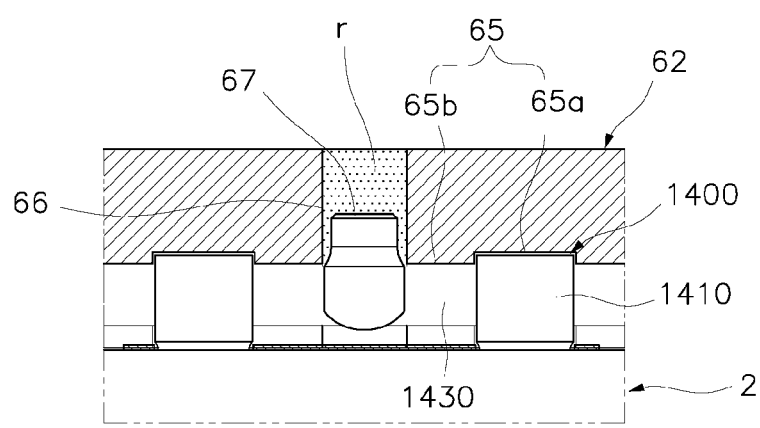
FIG. 17 is an exemplary view illustrating a process of fixing a clip according to one embodiment of the present invention.

FIG. 17 is an exemplary view illustrating a process of fixing a clip according to one embodiment of the present invention.

Referring to FIG. 17, mount parts 65 are formed on the inner surface portion of the artificial gum part 62 on the basis of the virtual holder device m40, and the artificial gum part 62 is manufactured to include a fixing hole 66 communicating with the mount parts 65. The mount part 65 includes a first engagement part 65a corresponding to an external form of the holder abutment 1410 and a second engagement part 65b corresponding to an external form of the fixing bar 1430, and thus is stepped. Accordingly, when the artificial gum part 62 is coupled to the holder device 1400, positions thereof may be aligned. In addition, an end portion of the clip 67 is inserted into the fixing hole 66, is fixed by a resin r which fills the fixing hole 66, and is cured. Accordingly, when the clip 67 fixed into the mount part 65 is engaged with the fixing bar 1430, the artificial gum part 62 and/or the overdenture 60 is supported by the holder device 1400 so that a state in which the artificial gum part 62 and/or the overdenture 60 is mounted on the oral cavity may be maintained.

In this case, the clip 67 is engaged with the fixing bar 1430 at the preset position thereof, and when the artificial gum part 62 is mounted to insert the holder device 1400 into the mount part 65, the end portion of the clip 67 may be positioned to be inserted into the fixing hole 66. In addition, when the fixing hole 66 is filled with the resin r and the resin r is cured, the clip 67 may be fixed to the artificial gum part 62.

Alternatively, the artificial gum part 62 is mounted to insert the holder device 1400 into the mount part 65 and the clip 67 is inserted into the fixing hole 66 so that the artificial gum part 62 may be engaged with the fixing bar 1430. In addition, when the fixing hole 66 is filled with the resin r and the resin r is cured, the end portion of the clip 67 may also be fixedly buried in the fixing hole 66. In this case, the fixing hole 66 may pass therethrough to have an inner circumference greater than a cross-sectional area of the clip 67, and the clip 67 may be attached to a clip holder and enter the fixing hole 66.

It is preferable that the resin r is provided with a resin the same as a resin used to manufacture the artificial gum part 62. Accordingly, when the fixing hole 66 is filled with the resin r and the resin r is cured, a fixing force can be increased due to a high fusing property inclination between the same materials. In addition, an outer surface of the end portion of the clip 67 may be processed to have fine irregularities. Accordingly, as a contact area with the resin r is increased, an attachment force may be further increased. In this case, it is preferable that a rubber dam covering a surface of the restoration target gum part 2 covers the resin r to prevent the resin r from being moved toward the gum tissue before the resin r is cured.

As described above, the present invention is not limited to the above-described embodiments and may be variously modified by those skilled in the art without departing from the scope of the present invention, and such modifications fall within the scope of the present invention. The present invention provides the following effects through the above-described solutions.

First, a highly precise dental restoration plan can be set for a patient on the basis of a scanning image and a CT image of an oral cavity and exterior information of implant and sleeve devices prestored in a digital library, and implanting guide devices and a dental restoration designed and three-dimensionally printed according to the plan can be highly accurately and precisely mounted in an oral cavity.

Second, implantation information is accurately set on the basis of the CT image on which a transverse section of the oral cavity is displayed, and image data for real designing is easily converted to a STL file allowing the implanting guide devices to be three-dimensionally printed on the basis of a scanning image and virtual data which are related to surface data so that designing and manufacturing processes can be significantly reduced.

Third, since a virtual flat surface position which is a reference during flattening and cutting an alveolar bone is corrected and set in consideration of an allowance distance for interference with the alveolar bone when the surgical guide is mounted, a real surgical guide is precisely fixed to the oral cavity to guide an implant to be implanted so that implantation precision can be significantly improved.

Fourth, since positions of a virtual implant and a virtual sleeve are first considered in consideration of an occlusal plane and an occlusal vertical dimension of the patient, and the virtual flat surface is set, precision of design information of the dental restoration of which occlusal precision with respect to opposing teeth is improved and the implanting guide devices which accurately guide implantation thereof can be significantly improved.

Fifth, since zig bases provided for general purpose are individually coupled to holder abutments and guide coupling of coupling screws is guided in a state in which alignment directions of the adjacent zig bases are restricted to be parallel to preset the bent passage information, a coupling tolerance is substantially close to zero, and thus implantation precision can be significantly improved.

Sixth, since the dental restoration is fixedly mounted through a holder device fixed in a large arc area along a dental arch, occlusion stability is significantly improved, and since a single clip is actually engaged with the fixing bar, mounting convenience can be significantly improved.

As described above, the present invention is not limited to the above-described embodiments and may be variously modified by those skilled in the art without departing from the scope of the present invention, and such modifications fall within the scope of the present invention.

What is claimed is:

1. A method of implanting dental restoration, comprising:
   generating a three-dimensional planning image in a first operation in which a scanning image including three-dimensional exterior information of upper and lower jaws, of which at least one is a restoration target gum part, overlaps and matches to a computed tomography (CT) image, a plurality of pieces of implantation information of implants are set along a dental arch in the three-dimensional planning image, and an implanting guide device including a bone reduction guide configured to guide flattening of an alveolar bone and a surgical guide configured to guide implantation of the implants is designed and manufactured;
   flattening the alveolar bone in a second operation by being guided by the implanting guide device, the implants are implanted, and holder devices, which include holder abutments and a fixing bar fixed to through-insertion portions of the holder abutments, are fixed to upper sides of the implants;
   correcting a temporary denture in a third operation to be occluded between the upper and lower jaws to form a temporary mounting portion, into which the holder device is inserted, in an inner surface portion of the temporary denture softened to be deformed due to an occlusal pressure to correspond to an occlusal vertical dimension of a patient when heated with a temperature within a preset softening temperature range;
   obtaining a corrected scanning image corrected to expose three-dimensional exterior information of the temporary mounting portion to an outside in a fourth operation from a scanning image of the temporary denture, and the three-dimensional exterior information of the temporary mounting portion is replaced and swapped with a virtual holder device; and
   forming a mount part in a fifth operation in an inner surface portion of an artificial gum part on the basis of the virtual holder device, and an artificial tooth part is fixed to the artificial gum part to which a clip engaged with the fixing bar is fixed to manufacture a dental restoration,
   wherein the first operation includes:
   virtually disposing a virtual implant selected from a digital library on the basis of the CT image to correspond to the implantation information, and
   virtually and concentrically disposing a virtual implanting guide sleeve to be spaced upward from an upper end portion of the virtual implant by an offset distance, wherein the virtual implanting guide sleeve and the scanning image overlap and are integrally stored; and
   generating design information of the surgical guide, wherein a virtual coupling hole corresponding to an outer circumference of the virtual implanting guide sleeve is formed in the design information.

2. The method of claim 1, wherein the first operation includes:
extracting an erasification model matching to the restoration target gum part from a plurality of erasification models standardized in a semi-cylindrical shape corresponding to an anatomical dentition stored in the digital library; and
erasing a portion, which overlaps the erasification model, in three-dimensional exterior information of the restoration target gum part to form a virtual flat surface.

3. The method of claim 2, wherein the first operation includes forming a contour of an inner surface portion of the bone reduction guide on the basis of the three-dimensional exterior information of the restoration target gum part, and design information of the bone reduction guide on which a flattening guide surface is formed along an edge opening at a position corresponding to the virtual flat surface.

4. The method of claim 3, wherein the first operation includes:
virtually displaying the extracted erasification model on the basis of an occlusal plane between the upper and lower jaws, and at least one surface is virtually adjusted to correspond to a second reference surface spaced downward from a first reference surface corresponding to an upper end portion of the virtual implant by a preset allowance distance; and
virtually correcting the virtual flat surface to correspond to the second reference surface.

5. The method of claim 4, wherein, in the first operation, the allowance distance is set in consideration of three-dimensional exterior information in which the virtual implant protrudes downward from the first reference surface to separate an inner surface of the surgical guide manufactured on the basis of the design information of the surgical guide from an outer surface of the flattened alveolar bone.

6. The method of claim 4, wherein the first operation includes:
virtually disposing a virtual abutment corresponding and matching to the offset distance; and
virtually correcting one surface of the erasification model to correspond to the second reference surface set to correspond to a position of a lower surface portion of the virtual abutment.

7. The method of claim 4, wherein, in the design information of the surgical guide in the first operation, a contour of an inner surface portion of the surgical guide is formed on the basis of three-dimensional exterior information of the restoration target gum part and the virtual flat surface.

8. The method of claim 4, wherein, in the design information of the surgical guide in the first operation, a contour of an inner surface portion of the surgical guide is formed on the basis of a contour of an outer surface portion of the bone reduction guide.

9. The method of claim 4, wherein, in the first operation, the design information of the surgical guide is generated to include:
forming a contour of an inner surface portion of the surgical guide on the basis of three-dimensional exterior information of the restoration target gum part and a virtual guide body part is set in which a virtual coupling hole corresponding to an outer circumference of the virtual implanting guide sleeve is formed;
virtually disposing a plurality of virtual cut blocks having a three dimensional form and protruding to have a thickness so as to match one surface of the surgical guide to the first reference surface and match an other surface thereof to the second reference surface along a circumference of the guide body part; and
erasing an overlapping region of the virtual cut blocks and the virtual guide body part to form a cut slot hole so as to form a first body part, which is a lower side of a divided one of a pair of manufactured real surgical guides, as the bone reduction guide.

10. The method of claim 1, wherein the first operation includes:
overlapping and matching the scanning image to the CT image on the basis of a preset occlusal plane;
virtually disposing a plurality of virtual implants selectively extracted from a digital library along a dental arch to align upper end portions of the plurality of virtual implants with a first reference surface spaced apart from the occlusal plane to correspond to a preset occlusal vertical dimension;
extracting one erasification model matching to the restoration target gum part from a plurality of erasification models standardized in a semi-cylindrical shape corresponding to an anatomical dentition and stored in the digital library;
virtually disposing the extracted erasification model to match one surface thereof to the occlusal plane and match the other surface thereof to the first reference surface, and an overlapping portion of the three-dimensional exterior information of the restoration target gum part and the erasification model is erased to virtually replace an upper side of the restoration target gum part in the three-dimensional exterior information of the restoration target gum part with a virtual flat surface; and
setting design information of the bone reduction guide and the surgical guide configured to guide flattening of the alveolar bone and implanting of the implant on the basis of the three-dimensional exterior information of the restoration target gum part and the virtual flat surface and design information of a dental restoration.

11. The method of claim 1, wherein:
the first operation includes setting bent passage information of the fixing bar so that both end portions are bent at preset angles and setting implantation information of the implant to correspond to implantation points, which pass the bent passage information, of a front tooth side and a molar tooth side; and
the second operation includes preparing fixing zig bases in which an alignment protrusions engaged with the through-insertion portions are formed on inner circumferences of accommodation grooves to operate in conjunction with the holder abutments and pivot guide zig bases rotatably supported by the holder abutments,
aligning a pair of holder abutments disposed to correspond to the implantation points of the front tooth side by a pair of the fixing zig bases such that the through-insertion portions linearly communicate with each other and fixing the pair of holder abutments to the front tooth side,
replacing and coupling the pivot guide zig bases to the holder abutments fixed to the front tooth side, and the fixing zig bases are coupled to upper end portions of the holder abutments disposed to correspond to the implantation points of the adjacent molar tooth side, and
fixing the holder abutments supported by the fixing zig bases rotated and restricted to linearly communicate with alignment grooves of the pivot guide zig bases to the molar tooth side.

12. The method of claim 11, wherein the second operation includes:
   recoupling and integrally connecting the fixing zig bases and the upper end portions of the holder abutments, which are fixed to the front tooth side and molar tooth side, to each other by a curable resin;
   inserting holder analogs, in which angle alignment parts corresponding to the through-insertion portions are formed, into the accommodation grooves to be integrally connected by the curable resin; and
   simultaneously inserting a fixing bar bent to correspond to the bent passage information into the angle alignment parts of the integrally connected holder analogs to determine and correct a bending error.

13. The method of claim 1, wherein, the fifth operation includes:
   mounting the artificial gum part, in which a fixing hole communicating with the mount part is formed to pass therethrough, in an oral cavity in which the holder device is mounted; and
   burying an end portion of the clip fixed to the fixing bar by a resin filling the fixing hole and cured to fix the clip to the artificial gum part.

14. The method of claim 1, wherein:
   the first operation includes virtually disposing a virtual base gum part, of which a contour of an inner surface portion corresponds to three-dimensional exterior information of the restoration target gum part, and setting an intersecting and overlapping portion of a virtual tooth and the virtual base gum part, which exceeds an occlusal vertical dimension, as an erasification region, and
   setting virtual engagement surfaces along an inner circumference from which the erasification region is erased, a cutting guide including cutting holes formed in the virtual engagement surfaces to pass therethrough, and designing and manufacturing the artificial gum part including coupling grooves corresponding to the virtual engagement surfaces; and
   the fifth operation includes hooking and engaging one side of an outer circumference of the artificial tooth part with an inner circumferential surface of each of the cutting holes of the cutting guide, and
   cutting and correcting an end portion of a dental root of the artificial tooth part protruding toward a side of an inner surface portion of the cutting guide to correct a height of the artificial tooth part to correspond to the occlusal vertical dimension on the basis of an inner edge of the cutting hole.

* * * * *